United States Patent [19]

Barney et al.

[11] Patent Number: 5,462,526

[45] Date of Patent: Oct. 31, 1995

[54] FLEXIBLE, STERILE CONTAINER AND METHOD OF MAKING AND USING SAME

[75] Inventors: Ward W. Barney, Mission Viejo; Steven L. Smith, Lake Forest, both of Calif.

[73] Assignee: McGaw, Inc., Irvine, Calif.

[21] Appl. No.: 121,614

[22] Filed: Sep. 15, 1993

[51] Int. Cl.$^6$ ....................................................... A61M 1/00
[52] U.S. Cl. ............................ 604/85; 604/403; 604/408; 604/410; 604/416; 604/56; 604/82; 604/87; 604/88; 604/90
[58] Field of Search ...................... 604/56, 82–92, 604/403–404, 408–410, 416; 128/DIG. 24

[56] References Cited

U.S. PATENT DOCUMENTS

| | | |
|---|---|---|
| 2,847,007 | 8/1958 | Fox . |
| 2,971,851 | 2/1961 | Kurtz . |
| 3,087,606 | 4/1963 | Bollmeier et al. . |
| 3,342,324 | 9/1967 | Piazze . |
| 3,343,664 | 9/1967 | Poitras . |
| 3,367,785 | 2/1968 | Finucane et al. . |
| 4,410,321 | 10/1983 | Pearson et al. . |
| 4,443,219 | 4/1984 | Meisch et al. . |
| 4,458,811 | 7/1984 | Wilkinson . |
| 4,467,588 | 8/1984 | Carveth . |
| 4,509,642 | 4/1985 | Rowell . |
| 4,511,533 | 4/1985 | Guadagno et al. . |
| 4,519,499 | 5/1985 | Stone et al. . |
| 4,534,509 | 8/1985 | Holzner . |
| 4,548,606 | 10/1985 | Larkin . |
| 4,602,910 | 7/1986 | Larkin . |
| 4,608,043 | 8/1986 | Larkin . |
| 4,610,684 | 9/1986 | Knox et al. . |
| 4,776,455 | 10/1988 | Anderson et al. . |
| 4,856,651 | 8/1989 | Francis, Jr. . |
| 4,997,083 | 3/1991 | Loretti et al. . |
| 4,998,671 | 3/1991 | Leifheit . |
| 5,102,408 | 4/1992 | Hamacher . |
| 5,176,634 | 1/1993 | Smith et al. . |
| 5,267,646 | 12/1993 | Inoue et al. . |

FOREIGN PATENT DOCUMENTS

| | | |
|---|---|---|
| 2099391 | 11/1981 | United Kingdom . |
| 9202271 | 2/1992 | WIPO ........................ 604/82 |
| WO9321890 | 11/1993 | WIPO . |

Primary Examiner—Randall L. Green
Assistant Examiner—P. Zuttarelli
Attorney, Agent, or Firm—Christie, Parker & Hale

[57] ABSTRACT

A flexible, sterile container is provided for sterile storing and mixing of medicaments and liquids which includes a shell with at least one compartment. At least one sterile liquid-containing pouch is in one of the compartments, and a medicament is in the compartment with the pouch or is in a different compartment. The liquid and medicament are mixed together by squeezing the shell and pouch to rupture the pouch to release the liquid for mixing with the medicament just prior to dispensing the mixture.

23 Claims, 4 Drawing Sheets

FLEXIBLE, STERILE CONTAINER AND METHOD OF MAKING AND USING SAME

FIELD OF THE INVENTION

The present invention relates to the field of flexible, sterile containers for storing and mixing medicaments and liquids in a sterile environment and for dispensing mixtures thereof. More particularly, the invention provides a flexible, sterile container which may be assembled in a sterile environment to provide a sterilized container in which liquids and medicaments may be stored separately until ready for mixing and dispensing.

BACKGROUND OF THE INVENTION

Various medicament (drug) solutions are commonly administered intravenously (via IV) from sterile containers to patients. Oftentimes, such solutions comprise a mixed combination of a liquid diluent, e.g., an aqueous dextrose or NaCl solution, and a medicament. Desirably, the medicament and diluent are stored separately in the container under aseptic conditions and are not mixed together until immediately prior to use so as to prevent degradation of the final product. Common packaging of the diluent and medicament is complicated by the nature of the medicament, which is often a powder which is sensitive to moisture contamination, or a powder or liquid sensitive to degradation under light or oxygen exposure.

Various multiple compartment containers have been disclosed which are used for aseptic storage and mixing of diluents and medicaments. For example, such containers are disclosed in U.S. Pat. No. 4,608,043 (Larkin) and U.S. Pat. No. 5,176,634 (Smith et al). U.S. Pat. Nos. 4,608,043 and 5,176,634 are incorporated herein in their entirety by this reference. The compartments of the containers disclosed in the foregoing patents are separated from each other by frangible heat seals. The seals are ruptured by manipulation of the container so that the contents of the compartments can be mixed together to thereby form a solution which is delivered to the patient through a standard IV arrangement.

The design of the containers of the '043 and '634 patents results in the sterilization process being more complex and, thus, more expensive than it needs to be. The complications with the sterilization process arise, in part, because of the Federal Food and Drug Administration (FDA) requirement that a level of sterility be achieved which is at least as high as the level achieved by the current practice of terminal steam sterilization. Achieving this high level of sterility is not possible with current aseptic liquid-fill technology. Therefore, to meet the FDA requirement, after a container has been filled with a liquid and sealed, it must be sterilized, i.e., it must undergo a terminal or final sterilization procedure.

Thus, the containers disclosed in the '043 and '634 patents must be sterilized either (1) after both the powdered medicament and diluent are in place in their respective sealed compartments or (2) after the diluent is in its sealed compartment while the medicament compartment remains empty. Both such processes present difficulties. In the first process, the container is fabricated with the diluent and medicament compartments unfilled and open for receiving the diluent and the medicament, respectively. The container is then sterilized, e.g., by radiation, and the diluent and medicament are aseptically filled into the two sterilized compartments and the compartments are sealed. Because of the aforementioned FDA requirement, the container and its contents must then be sterilized again, i.e., the container must undergo a final or terminal sterilization. One form of such final sterilization is to use steam in an autoclave process. Because powdered medicaments can be degraded to some degree by moisture or heat, the use of steam for final sterilization is not optimum. Furthermore, because such containers use film materials which are designed to protect powdered medicaments from moisture and atmospheric gases, it takes longer for steam to penetrate the film to provide its sterilization function, resulting in process inefficiencies.

Although such containers with a diluent sealed therein could undergo final sterilization with radiation, several problems are encountered with such a process. Firstly, dextrose diluents are degraded by radiation. Secondly, when aqueous solutions are irradiated, undesirable peroxides can be formed. The use of ethylene oxide (EtO) instead of radiation for final sterilization is not possible because the EtO gas will not effectively penetrate the films from which the containers are constructed. Thus, neither radiation nor EtO sterilization can be used to eliminate the problems which are described above as being associated with the autoclave process.

If final sterilization of the containers of the '634 and '043 patents is done after the diluent is in its respective compartment, but before the powdered medicament is in place, other problems may result. For example, if the container is steam sterilized (autoclaved) with the medicament compartment empty, moisture can become entrapped in the medicament compartment and/or within the film structure. Because such moisture can damage the medicament which is to be filled into the compartment, the compartment should be dried before the medicament is placed therein. This results in extra processing steps and additional expense. Furthermore, the same problems which are described above, with regard to sterilizing the container using radiation or EtO, are present if such radiation or EtO were to be used as a sterilization step for a container which contains a diluent in the absence of a medicament.

In view of the foregoing, it can be seen that there is a need for a sterile medicament container which is designed to eliminate the requirement that it undergo final sterilization after a liquid diluent is sealed in place therein.

SUMMARY OF THE INVENTION

The present invention provides the advantages of containers having one or more sterile compartments in which medicaments and liquids may be separately stored, but in a way that eliminates the need for the container to be sterilized after the liquid has been placed into and sealed in its respective compartment.

In accordance with a preferred embodiment of the present invention, there is provided a flexible, sterile container which comprises a flexible shell with a sterile interior, at least one sterile compartment within the shell, at least one sterile self-contained flexible pouch containing a liquid disposed within one of said compartments and at least one medicament also disposed within one of said compartments. The liquid and medicament may be mixed together by rupturing the pouch within the sterile interior of the container to release liquid which is subsequently mixed with the medicament just prior to use. The mixture can be dispensed from the container through suitable nozzles or other known dispensing means.

To provide the container of the present invention, an empty pouch is filled with a desirable liquid, e.g., a diluent, and is then sealed and sterilized, e.g., in an autoclave, to comply with FDA requirements. The pre-sterilized pouch and sterile shell components of the container are then brought together in a sterile environment for assembly. The sterile pouch may be placed into the empty sterilized container shell, or into one compartment of a sterilized shell, which can then be aseptically filled with a pre-sterilized medicament, either directly within the shell containing the flexible pouch or into a separate sterile compartment adjacent the compartment containing the liquid-filled pouch within the shell. Where two or more sterile compartments are used in this manner, a removable seal, e.g., a peelable seal, is provided at the juncture between compartments. It is also possible to provide a three-compartment system in which the liquid-filled pouches are placed in one compartment of a shell adjacent a second compartment in which the medicament is disposed and a third compartment adjacent the second compartment. The third compartment is separated from the second compartment by a removable seal and is provided to receive the mixture for dispensing. In the latter configuration, rupturing the liquid-filled pouch(es) and removing the seal between the compartment containing the pouch and the compartment containing the medicament allows the medicament and diluent to be mixed, after which the mixture may be moved into the third compartment, from which the mixture may be dispensed as needed, by opening the seal between the second and third compartments.

An important feature of the present invention is the elimination of the requirement that the container be sterilized after the liquid diluent is in place therein and the compartment containing the diluent has been sealed.

BRIEF DESCRIPTION OF THE DRAWINGS

These and other features, aspects, and advantages of the present invention will be more fully understood when considered with respect to the following detailed description, appended claims, and accompanying drawings, wherein:

DETAILED DESCRIPTION

Figures 1, 2:
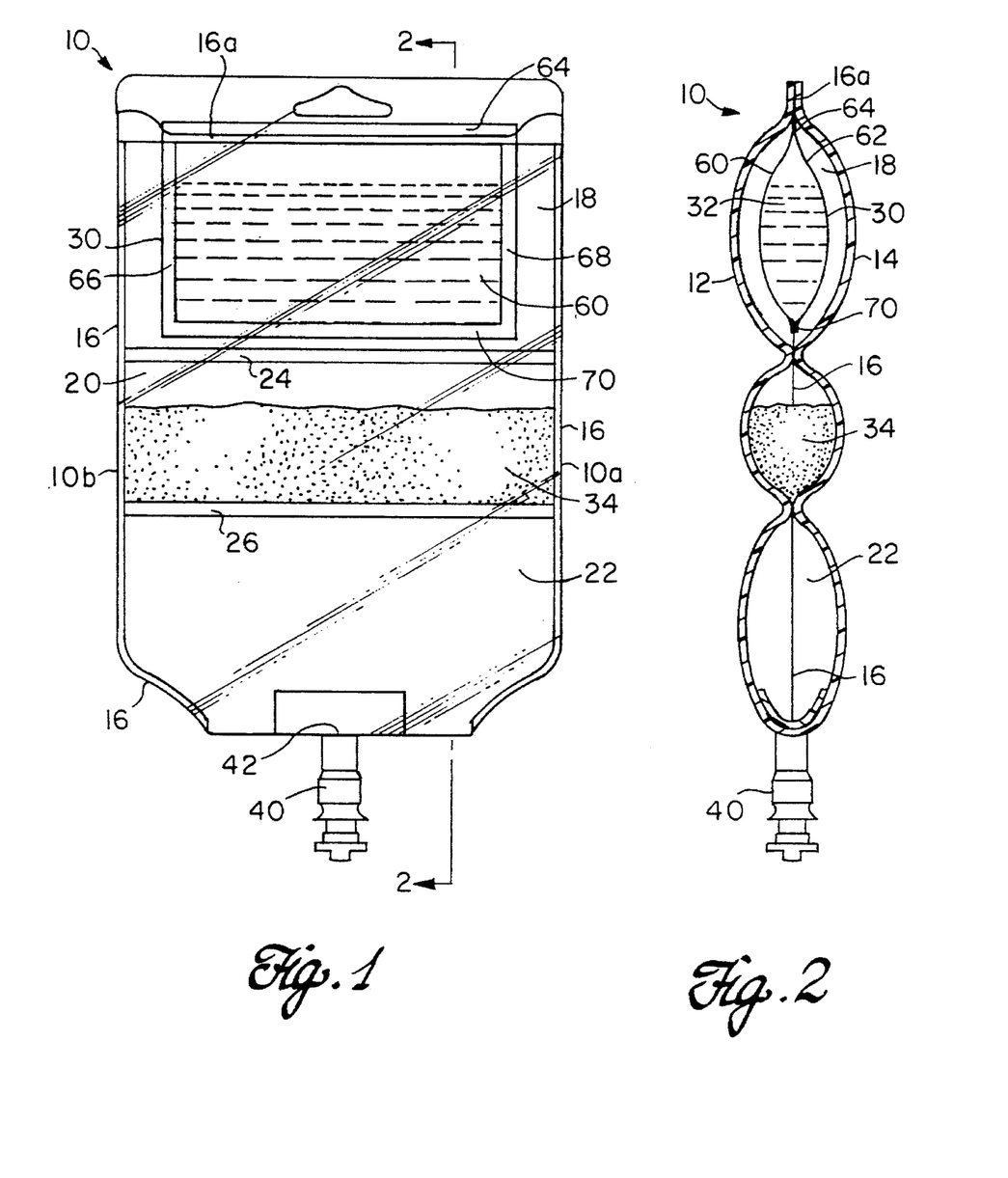
FIG. 1 is a schematic front view of one preferred embodiment of a three-compartment container provided in accordance with practice of the present invention in which a liquid-filled pouch is disposed in one compartment adjacent a second compartment in which medicament is disposed, which in turn is adjacent a third compartment into which a mixture of liquid and medicament will be caused to flow for ultimate dispensing as needed, with intermediate removable seals between adjacent compartments.
FIG. 2 is a schematic cross-sectional view taken along line 2—2 of FIG. 1.

Referring to FIGS. 1 and 2, there are shown schematic front and cross-sectional side views, respectively, of a preferred embodiment of a flexible, sterile container 10 provided in accordance with practice of the present invention. Although the container 10 can be viewed in any orientation, for purposes of exposition herein, the position of the components of the container relative to each other are described as shown in FIGS. 1 and 2. The container 10 is formed from a front sheet 12 and a back or rear sheet 14 (shown only in FIG. 2), which may be laminates of flexible material, to be described in greater detail below. The sheets forming the container can be provided separately and then sealed together at their common peripheral edge by means of an edge seal which extends around the entire periphery of the container. Conversely, the front and rear sheets can be formed from a single film sheet folded at its bottom and sealed together, for example, by means of a heat seal 16, which extends around the side and top portions of the container, as shown in FIG. 1. The sealed-together sheets are referred to herein as the "shell" of the container.

In the present embodiment, the container 10 is partitioned into three separate compartments; an upper compartment 18, an intermediate compartment 20, and a lower or outlet compartment 22, each of which is sterile. The upper and intermediate compartments 18 and 20 are separated from each other by a first removable seal 24, and the intermediate and lower compartments 20 and 22 are separated from each other by a second removable seal 26. The removable seals 24 and 26 extend between the two sides of the container, i.e., between the right side 10a and the left side 10b, joining the front and rear sheets. While it is presently preferred that the removable seals between compartments are peelable seals, which are described below in greater detail, and which are provided by well-known heat sealing methods, other types of sealing arrangements can be used, if desired.

Additional details of the structure and fabrication of medicament containers which incorporate multiple compartments separated by peelable seals are disclosed in U.S. Pat. No. 5,176,634, which is incorporated by reference above.

A sterile, flexible pouch 30 containing a liquid diluent 32 is disposed in the upper compartment 18, and a powdered medicament 34 is disposed in the intermediate compartment 20. As is described below in greater detail, the lower or outlet compartment 22 of the present embodiment of the container 10 remains empty until the container is used. An outlet port 40, for dispensing the contents of the container 10, subsequent to mixing of the medicament and diluent as is described below, extends through an opening 42 in the bottom of the outlet compartment 22.

Figure 3:
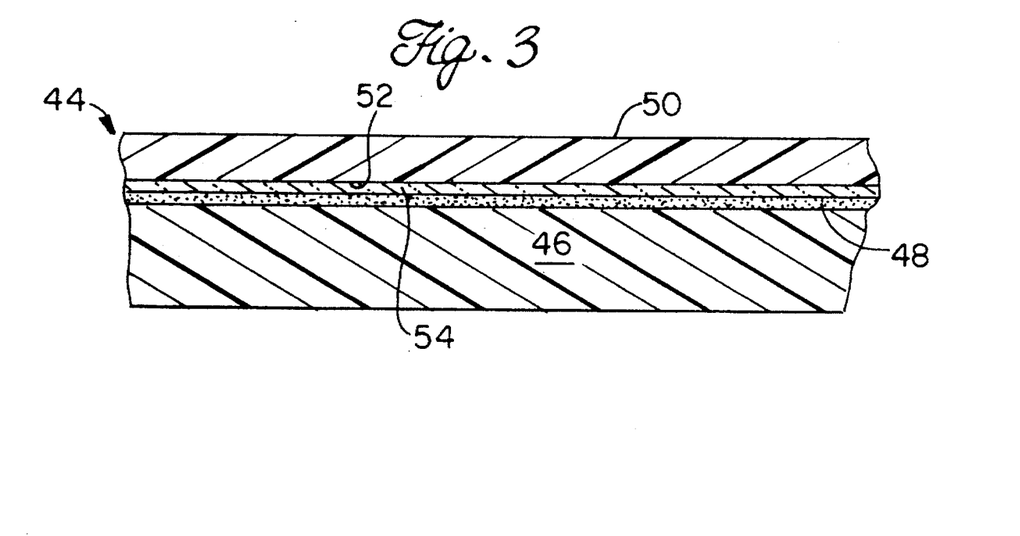
FIG. 3 is a schematic cross-sectional view of a presently preferred laminated film structure used in fabricating a container provided in accordance with practice of the present invention.

In one embodiment of the present invention, the front and back sheets 12 and 14, respectively, are composed of a multi-layered, laminated film 44, which is shown in schematic cross-section in FIG. 3. The film 44 comprises an inert sealant layer 46 on its inwardly facing surface, for example, a 6-mil-thick polyolefin-synthetic elastomer composition (20% Kraton®, 80% polypropylene polyethylene copolymer), which is bonded by means of an appropriate adhesive 48 to a 48-gauge, bi-axially oriented polyester film 50. (Kraton® is a 20% styrene butadiene elastomer rubber produced and marketed by Shell Chemical Corporation.) Preferably, the polyester film is coated on its inside surface 52 with a high moisture and oxygen barrier material 54, such as $SiO_x$, which takes the form of a "clear glass coating." Coatings such as aluminum oxide ($Al_2O_3$) may be used in place of $SiO_x$, if desired. Other films which may be useful to provide the front and back portions of the shell of the container 10 of the present invention are disclosed in U.S. Pat. Nos. 5,176,634 and 4,803,102, which are incorporated herein by this reference or by prior reference.

Figure 4:
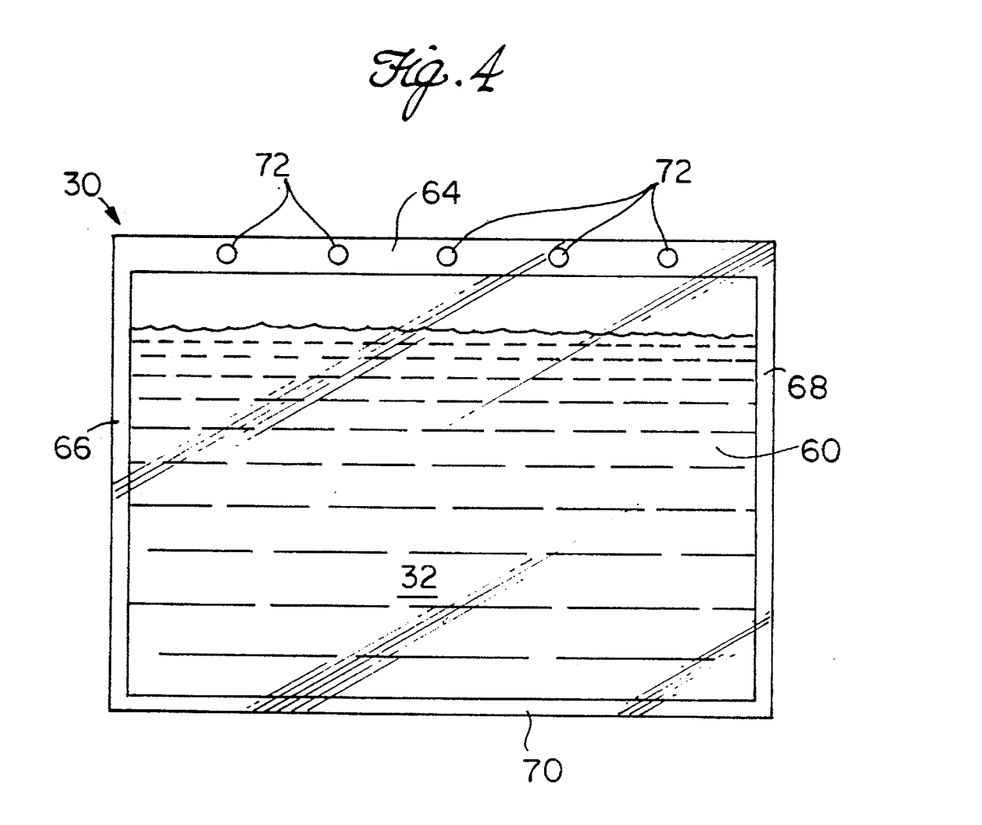
FIG. 4 is a schematic front view of a sterile, liquid-filled pouch configured to be disposed in one compartment of a medicament container provided in accordance with practice of the present invention.

Turning to FIG. 4, in addition to FIGS. 1 and 2, in an exemplary embodiment, the pouch 30 (which is shown apart from the container in FIG. 4) is filled with a dextrose or a saline diluent 32 and is made from front and back facing sheets 60 and 62 of a polymeric film. In a preferred embodiment, each of the film sheets 60 and 62 is a multiple layer film which comprises an inwardly facing 6-mil-thick polyolefin-synthetic elastomer composition (20% Kraton®, 80% polypropylene copolymer), co-extruded with a 1-mil-thick, relatively higher-melting-temperature polypropylene on its outwardly facing surface. Alternatively, each of the film sheets 60 and 62 may be the same as the film 44 described above as the preferred film for constructing the shell of the container 10. Having a high barrier film such as the laminated film 44 will minimize the amount of moisture which can escape from the diluent through the pouch walls. Additionally, if desired, the pouch material can be a monolayer film of polypropylene or polyethylene, or other appropriate material.

In one embodiment, the sheets 60 and 62 forming the pouch are sealed together around their common peripheral edge by means of heat seals. Preferably, the heat seal 64 along the top edge and the heat seals 66 and 68 along the side edges are relatively stronger than the heat seal 70 along the bottom edge, which is preferably provided as a peelable seal. Thus, the peelable seal 70 is configured to be ruptured by hydraulic pressure generated in the pouch by squeezing the upper compartment portion of the container shell with a force of sufficient magnitude, while the seals 64, 66 and 68 remain intact. Although the peelable seal 70 is along the bottom edge of the pouch in this embodiment, it is contemplated that the peelable seal could also be along one of the other edges. While in the above-described embodiment, the diluent fluid escapes from the pouch through a ruptured peelable seal, other arrangements can be provided for escape of the fluid. For example, in another preferred embodiment, a weakened zone is provided in the film from which the pouch is constructed adjacent one of the peripheral heat seals at the time the heat seals are formed. The weakened zone is ruptured at the appropriate time by hydraulic pressure generated by squeezing the upper compartment portion of the container shell. In another preferred embodiment of the container of the present invention, a weakened section is provided on the surface of the pouch material by means of a score line. In this embodiment, the liquid diluent escapes from the pouch through the score line after sufficient hydraulic pressure is generated by squeezing the container to rupture the pouch material at the score. In yet another embodiment, the pouch is fitted with a valving arrangement, wherein the valve is closed by a blow-out plug which is forced from the valve at the desired time by hydraulic pressure generated in the pouch by squeezing the compartment of the container shell in which the pouch resides. Other valving means known in the art can be used, if desired, to provide the hydraulically actuated release of liquid from the pouch.

Preferably, the pouch 30 is permanently connected to a top portion of the container 10. In one exemplary embodiment, the top peripheral heat seal 64 of the pouch 30, which is in the form of a flange, is permanently bonded, i.e., is trapped, between the container's front and rear sheets 12 and 14, respectively, by means of the heat seal 16a along the top portion of the container. If desired, a plurality of holes 72 (shown in FIG. 4) are provided through the upper heat seal flange 64. The bond between the pouch flange 64 and the container 10 is strengthened by the provision of the holes 72 as a result of material from the facing layers of the sheets 12 and 14 flowing through the holes 72 and bonding together during the process by which the heat seal 16a is formed along the container top. Alternatively, when the material comprising the pouch heat seal flange 64 is not compatible for forming a heat bond with the material comprising the inwardly facing layers of the container sheets 12 and 14, the pouch flange 64 can be sufficiently bonded or trapped into the heat seal 16a by the material of the sheets 12 and 14 bonding together through the holes 72.

It should be noted that, in this and the other illustrated embodiments, the medicament is disclosed as being in the form of a powder. However, a liquid medicament may be employed in this system, where the liquid medicament and the liquid diluent are not compatible for long periods of time and must be mixed just prior to dispensing to a patient. Furthermore, while a single sterile, rupturable pouch 30 is disclosed as being housed within the upper compartment 18, if desired, multiple sterile pouches having the same diluent, or multiple pouches with different diluents, may be used. Furthermore, one or more pouches provided in accordance with the present invention may be filled with a liquid medicament.

Manufacture and Assembly of the Medicament Container

The composition of the front and rear sheets 12 and 14 of the container 10, and the composition of the front and rear sheets 60 and 62 of the pouch 30, allows for the creation of the peripheral heat seal 16 and the peelable seals 24 and 26 of the container and the peripheral heat seals 64, 66 and 68 and peelable seal 70 of the pouch by means of standard heat sealing techniques.

A "peelable" seal as used herein is a seal which is sufficiently durable to allow normal handling of the container or pouch, yet which will peel or separate substantially completely under pressure applied by manipulating the container and/or pouch, to thereby allow mixing and dispensing of the container contents. Peelable seals are formed by partial melting together of the polymer present in the adjacent layers of the front and rear facing sheets. Such seals are obtained by heat sealing with various times, temperatures and pressures as are known in the art. Conversely, the peripheral edge seal 16 of the container and the edge seals 64, 66, and 68 of the pouch are significantly stronger than the peelable seals and will not be ruptured by pressures generated to separate the peelable seals. Additional details of methods for forming heat seals and peelable seals are disclosed in U.S. Pat. No. 5,176,634.

During the manufacturing process, the outlet port 40 is attached by conventional means to the bottom portion of the lower compartment 22 of the container 10, while the top edge of the container's upper compartment 18 remains open to receive one or more sterile, filled and sealed diluent pouches. In an exemplary embodiment, at least one of the sides of the intermediate compartment 20 remains open to receive a powdered medicament.

The container, at the stage of manufacture where all of the compartments are empty, is, in one embodiment, sterilized in a sterile room, using radiation. After the empty container has been sterilized, the container's intermediate compartment 20 is sterile-filled (aseptically filled) with a powdered medicament, using standard sterile-fill techniques, and the medicament compartment is sealed, e.g., by heat sealing, to complete the peripheral seal 16 along the side of the container.

Pre-formed pouches, which are eventually filled with liquid, sealed, sterilized, and placed into the upper compartment 18, are formed of flexible polymer sheets which are heat sealed along a portion of their perimeter, for example, along the side and bottom edges, forming the heat seals 66, 68, and 70, leaving a top portion of the perimeter open to provide access for filling with a liquid diluent. As was mentioned above, in a preferred embodiment, the heat seal 70 is a peelable seal. The pouches are filled with a liquid diluent through their open tops, for example, with a dextrose or saline solution, and then the top edge of the pouch is sealed, for example, by means of heat sealing, to provide the upper seal flange 64. The liquid-filled pouches are then sterilized, in an exemplary embodiment, by means of an autoclave process, and are transported in a sterile environment to the sterile room where the medicament-filled sterile containers are located. One or more sterile, diluent-filled pouches 30 are then placed into the open upper compartment 18 of the container 10, and the upper compartment is sealed, using standard heat sealing techniques to thereby form the seal 16a. In a preferred embodiment, the pouch is placed in the open compartment 18 with the heat seal flange portion 64 of the pouch extending between the upper edges of the sheets 12 and 14. The heat seal 16a is formed along the upper edge of the container, thereby permanently bonding the heat seal flange 64 between the sheets 12 and 14. Although, in the illustrated embodiment, only one such pouch 30 is placed into the compartment 18, two or more pouches with the same or different diluents or containing a liquid medicament may be placed therein, if desired.

Although the above-described embodiment discloses that the medicament is aseptically sealed into the medicament compartment 20, followed by placement of the pre-sterilized diluent pouch 30 into the compartment 18, the process can be reversed. For example, in another preferred embodiment, the pre-sterilized diluent pouch or pouches 30 are placed and sealed into the compartment 18, and the medicament is then aseptically filled into the intermediate compartment 20. Filling of medicament can be in the same sterile room in which the pouch was inserted, or the container shell and pouch combination can be aseptically transported to another sterile location for aseptic filling with medicament.

A key feature of the present invention resides in disposing the diluent in the container's upper compartment in a pre-filled, sterile pouch instead of filling the diluent directly into the compartment. Because the diluent pouch and its contents are sterile prior to their emplacement in the container's upper compartment, there is no requirement that the assembled medicament container undergo a final sterilization after the diluent pouch has been sealed therein. This eliminates the problems that are described above as being associated with a final sterilization process.

Use of the Container

The container 10 will be received by healthcare personnel in the completed figuration shown in FIGS. 1 and 2. When the container is to be used, the upper compartment 18 is squeezed to thereby provide sufficient hydraulic pressure to rupture the peelable seal 70 of the diluent-filled pouch 30, so that the diluent escapes therefrom. Continued pressure on the compartment 18 produces a hydraulic force which ruptures the peelable seal 24 between the upper and intermediate compartments. Further manipulation of the container by shaking causes mixing of the liquid diluent and the powdered medicament. After complete mixing is accomplished, the peelable seal 26 between the intermediate and lower compartments is ruptured by hydraulic forces generated by further compressing the front and rear sheets of the container, so that the medicament solution flows into the container's lower or outlet compartment 22. The solution is then ready to be dispensed from the container 10 through the outlet port 40, using standard IV delivery equipment (not shown).

Figure 5:
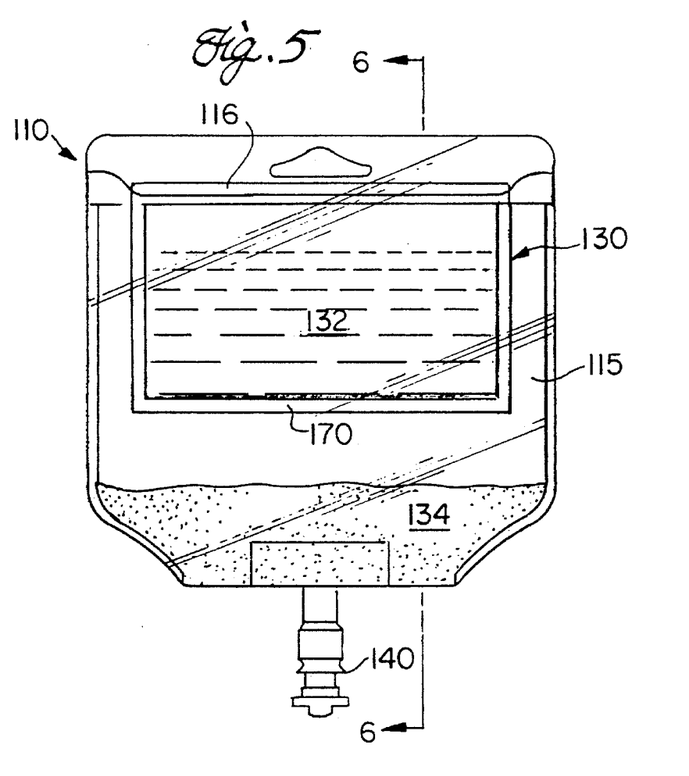
FIG. 5 is a schematic front view of a second preferred embodiment of a container provided in accordance with practice of the present invention showing a single compartment in which is disposed a liquid-filled pouch and medicament.
Figure 6:
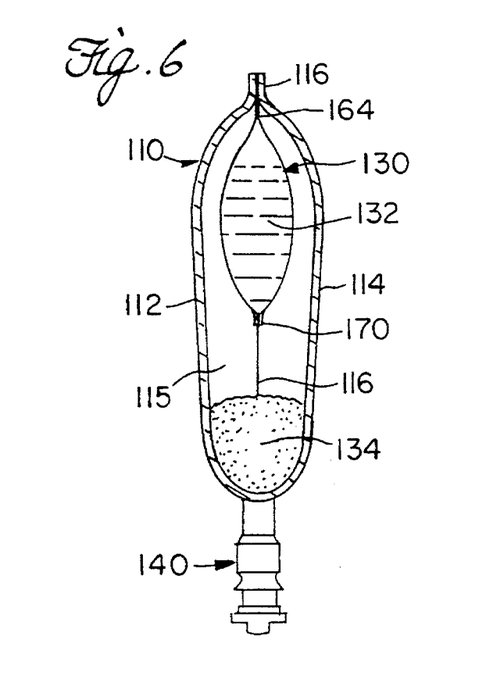
FIG. 6 is a schematic cross-sectional view taken along line 6—6 of FIG. 5.

While the container 10 shown in FIGS. 1 and 2 incorporates three compartments, containers having more or fewer than three compartments are contemplated. For example, turning to FIGS. 5 and 6, there is shown a preferred embodiment of a sterile medicament container 110 provided in accordance with practice of this invention which incorporates only a single sterile compartment 115. As was the case with the container disclosed with respect to FIGS. 1 and 2, the container of FIGS. 5 and 6 has laminated front and rear sheets 112 and 114 which are bonded together by peripheral edge seals 116 to form the container shell. A powdered medicament 134 is disposed in the compartment 115, and a sterile, flexible, rupturable pouch 130 containing a dextrose diluent 132 is in the compartment with the medicament. In one embodiment, the front and rear sheets 112 and 114 of the container 110 and the diluent-filled pouch 130 are constructed of the same materials as the front and rear sheets 12 and 14 and the pouch 30 disclosed in the embodiment of FIGS. 1 and 2. The pouch 130 is permanently attached to the top portion of the shell along the upper edge of the compartment 115 by means of the heat seal flange 164 along the top edge of the pouch being bonded between the upper interfacing edges of the sheets 112 and 114, i.e., being bonded or trapped within the upper edge seal 116.

In another embodiment of the container 110 of the present invention, the diluent pouch is constructed of the film material 44 described above for constructing the shell of the container 10. Fabricating a pouch from the film 44 with its associated high moisture barrier properties minimizes the escape of moisture from the pouch, thereby minimizing any possibility that the medicament 134 will be degraded by the escaped moisture.

To use the medicament container 110, the pouch 130 is ruptured along a peelable seal 170 along its bottom edge by squeezing the container 110 so that the liquid diluent 132 escapes from the pouch through the ruptured seal and is mixed together with the medicament 134 by further manipulation of the container. Upon complete dissolution of the medicament in the diluent, the solution is ready to be dispensed from the container 110 through the outlet port 140, using a standard IV delivery device (not shown).

Figure 7:
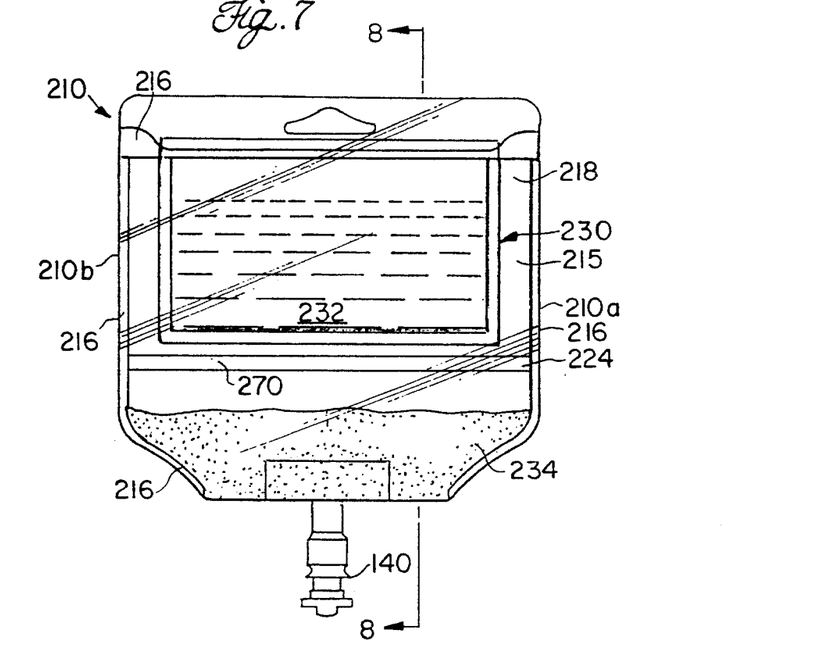
FIG. 7 is a schematic front view of a third preferred embodiment of a container provided in accordance with practice of the present invention comprising two compartments, wherein a liquid-filled pouch is disposed in one compartment and a medicament is disposed in the second compartment, and the compartments are separated by a removable seal.
Figure 8:
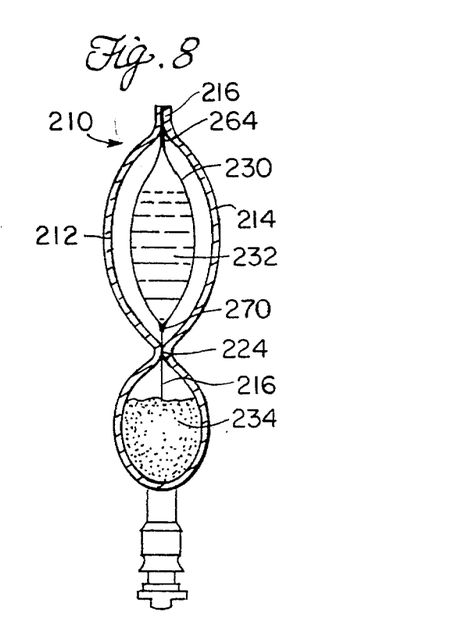
FIG. 8 is a schematic cross-sectional view taken along line 8—8 of FIG. 7.

Turning to FIGS. 7 and 8, there is shown yet another preferred embodiment of a container 210 provided in accordance with practice of the present invention which is formed from front and rear sheets 212 and 214 which are bonded together by peripheral edge seals 216. The container 210 comprises two compartments; a first or upper compartment 218, and a lower or outlet compartment 222, which are separated from each other by a peelable seal 224. The peelable seal 224 extends between the two sides of the container, i.e., between the right side 210a and the left side 210b, joining the front and rear sheets 212 and 214, respectively. A sterile, flexible pouch 230 containing a liquid diluent 232 is disposed in the upper compartment 218, and a powdered medicament 234 is disposed in the lower compartment 222.

In one preferred embodiment, the front and back sheets 212 and 214 and the diluent-filled pouch 230 are constructed of the same materials as the front and back sheets and the diluent pouch 30 of the container defined according to FIGS. 1 and 2. The pouch 230 is permanently attached along the upper edge of the compartment 218 by means of the heat seal flange 264 being bonded between the upper interfacing edges of the sheets 212 and 214, forming part of the upper edge seal 216.

The first step in using the container 210 is to squeeze the upper compartment 218 to thereby provide sufficient pressure to rupture the pouch 230 along a peelable seal 270 along its bottom edge, so that the liquid diluent 232 escapes therefrom. Continued pressure on the compartment 218 produces a hydraulic force which ruptures the peelable seal 224 between the upper and lower compartments. Further manipulation by shaking causes mixing of the liquid diluent and the powdered medicament. After the mixing is complete, the medicament solution is ready to be dispensed from the container 210 through the outlet port 240, using a standard IV delivery device (not shown).

As was mentioned above, a key feature of the present invention, and one that is associated with each embodiment thereof, is the elimination of a final sterilization step as a result of the diluent being provided in a sterile-filled pouch instead of being filled directly into the container.

Another advantage of the container of the present invention is the possibility of employing alternative embodiments thereof, using similar concepts. For example, in one alternative embodiment, the flexible front and back sheets may be composed of different materials, which may allow for greater latitude in developing peelable seals. Typical materials for construction may include polypropylene (PP) or polyethylene (PE) as inner sealant layers on one sheet with the paired sheet composed of a modified PP or PE (pursuant to standard well-known additive blends) selected so as to promote and enhance the peelable sealing characteristics of the heat-sealed welds formed between these materials when heat sealed.

The above descriptions of exemplary embodiments of flexible, sterile containers are for illustrative purposes. Because of variations which will be apparent to those skilled in the art, the present invention is not intended to be limited to the particular embodiments described above. For example, while the sterile, liquid-filled diluent pouches are shown as being permanently attached to the container, pouches may instead be loosely placed into the container. The scope of the invention is described in the following claims.

What is claimed is:

1. A flexible, sterile container for storing and mixing medicaments and diluent liquids in a sterile environment, and dispensing mixtures thereof, comprising:

a flexible shell having a top, bottom and sides with a sterile interior;

at least one sterile compartment within said shell;

at least one medicament disposed within said at least one sterile compartment;

at least one sterile, self-contained, flexible pouch containing a diluent liquid suspended within said at least one sterile compartment, wherein the sterile pouch is permanently connected along an upper edge to a top portion of the flexible containers, said flexible pouch being rupturable by application of pressure to the shell and pouch sufficient to release the liquid into the sterile compartment for subsequent mixing with said medicament without rupturing the shell; and dispensing means for dispensing a mixture of liquid and medicament from said container.

2. A flexible, sterile container according to claim 1 further comprising a plurality of self-contained flexible pouches containing liquid disposed within said at least one sterile compartment, each of said pouches being rupturable by application of pressure sufficient to rupture said pouches and release liquid contained therein into the sterile compartment for mixing with medicament, without rupturing the shell.

3. A flexible, sterile container according to claim 1, wherein the medicament is in dry powder form.

4. A flexible, sterile container according to claim 1, wherein the medicament is in liquid form.

5. A flexible, sterile container according to claim 1, wherein the diluent liquid is a dextrose solution.

6. A flexible, sterile container according to claim 1, wherein the diluent liquid is a saline solution.

7. A flexible, sterile container according to claim 1, wherein the pouch comprises a peelable seal along one of its edges and is rupturable along said peelable seal by application of pressure to the shell and pouch sufficient to release the liquid through the ruptured seal.

8. A flexible, sterile container according to claim 1, wherein the diluent pouch is formed from two facing polymeric sheets which are heat-sealed around their edges, and wherein a seal along the top edge of the pouch defines a flange, wherein said flange is permanently connected to a top portion of the shell.

9. A flexible, sterile container according to claim 8, wherein the container shell comprises front and rear polymer sheets which are bonded together around their perimeter, the pouch being connected to the top portion of the shell by means of the pouch seal flange being trapped within the perimeter bond between the sheets along a top portion of the container.

10. A flexible, sterile container according to claim 1, wherein the shell comprises a plurality of sterile compartments, further comprising:

at least one flexible, sterile diluent-containing pouch disposed within a first compartment and a medicament disposed in a second adjacent compartment, said flexible pouch being rupturable by application of pressure to the shell and pouch sufficient to rupture the pouch without rupturing the shell to release the diluent liquid contained in the pouch into the first sterile compartment;

a removable seal between adjacent compartments so that, upon removal of such seal, adjacent compartments are in fluid communication; and dispensing means to dispense a mixture of medicament and liquid.

11. A flexible, sterile container according to claim 10 comprising two sterile compartments containing liquid and medicament, respectively.

12. A flexible, sterile container according to claim 10 comprising three sterile compartments; a first compartment containing at least one flexible diluent-containing pouch, a second compartment adjacent said first compartment containing a powdered medicament, and an initially empty third compartment adapted to receive and contain a mixture of liquid diluent and medicament from the first and second compartments;

removable seals between the first and second compartments and between the second and third compartments; and dispensing means for dispensing a mixture of medicament and liquid diluent from the third compartment.

13. A flexible, sterile container according to claim 10, wherein the medicament is selected from a dry powder medicament and a liquid medicament.

14. A flexible, sterile container according to claim 10, wherein the sterile pouch is permanently connected along its upper edge to a top portion of the first compartment.

15. A flexible, sterile container according to claim 10, wherein the pouch comprises a peelable seal along one of its edges and is rupturable along said peelable seal by application of pressure to the shell and pouch sufficient to release the liquid through the ruptured seal.

16. A flexible, sterile container according to claim 10, wherein the diluent pouch is formed from two facing polymeric sheets which are heat sealed around their edges, and wherein a seal along the top edge of the pouch defines a flange, wherein said flange is permanently connected to that portion of the shell that defines the top portion of the first compartment.

17. A flexible sterile container according to claim 10, wherein the container shell comprises front and rear polymer sheets which are bonded together around their perimeters, the pouch being connected to the top portion of the shell by means of a sealed flange along the pouch top edge being trapped within the perimeter bond between the sheets along a top portion of said container.

18. A flexible, sterile container according to claim 17, wherein the flange of the pouch heat seal incorporates a plurality of holes therethrough, and material from the container perimeter bond has flowed through and bonded together through said holes.

19. A flexible, sterile container for storing and mixing medicaments and diluent liquids in a sterile environment, and dispensing mixtures thereof, comprising:

a flexible shell having top, bottom and sides defining three sterile compartments and formed from front and back facing polymeric sheets wherein each of said sheets has a perimeter therearound, a first of said compartments at the top of the shell containing at least one flexible, sterile, diluent-filled pouch, a second of said compartments adjacent the first compartment containing a sterile powdered medicament, and an initially empty third compartment at the bottom of the shell adapted to receive and contain a mixture of the liquid diluent and the medicament from the first and second compartments;

a heat seal provided around the perimeter of the flexible sheets, bonding said flexible sheets together, and peelable seals between the first and second compartments and between the second and third compartments, said pouch being heat sealed along one edge and having a peelable seal along another edge, wherein the heat seal forms a flange which is connected to an upper edge of the first compartment; and dispensing means for dispensing a mixture of medicament and liquid diluent from the third compartment.

20. A flexible, sterile container according to claim 19, wherein the medicament is selected from a dry powder medicament and a liquid medicament.

21. A flexible, sterile container according to claim 19, wherein the diluent liquid is a selected from a dextrose solution and a saline solution.

22. A flexible, sterile container according to claim 19, wherein the flange of the pouch heat seal incorporates a plurality of holes therethrough, and material from the container perimeter heat seal at the upper edge of the first compartment has flowed through and bonded together through said holes.

23. A flexible, sterile container for storing and mixing medicaments and diluent liquids in a sterile environment, and dispensing mixtures thereof, comprising:

a flexible shell having a top, bottom and sides with a sterile interior;

a plurality of sterile compartments within said shell;

at least one flexible, sterile diluent-containing pouch suspended within a first sterile compartment and a medicament disposed in a second adjacent sterile compartment, said flexible pouch being rupturable by application of pressure to the shell and pouch sufficient to rupture the pouch without rupturing the shell to release the diluent liquid contained in the pouch into the first sterile compartment;

a removable seal disposed between adjacent compartments so that, upon removal of such seal, adjacent compartments are in fluid communication; and dispensing means to dispense a mixture of medicament and liquid from said container.

\* \* \* \* \*